(12) United States Patent
Reinke et al.

(10) Patent No.: US 9,201,016 B2
(45) Date of Patent: Dec. 1, 2015

(54) DEVICE FOR THE CONTACTLESS AND NONDESTRUCTIVE TESTING OF SURFACES

(71) Applicant: WINTERTHUR INSTRUMENTS AG, Winterthur (CH)

(72) Inventors: Nils Reinke, Winterthur (CH); Andor Bariska, Zürich (CH)

(73) Assignee: WINTERTHUR INSTRUMENTS AG, Winterthur (CH)

( * ) Notice: Subject to any disclaimer, the term of this patent is extended or adjusted under 35 U.S.C. 154(b) by 0 days.

(21) Appl. No.: 14/280,999

(22) Filed: May 19, 2014

(65) Prior Publication Data

US 2014/0252232 A1   Sep. 11, 2014

Related U.S. Application Data

(63) Continuation of application No. 13/642,956, filed as application No. PCT/CH2011/000097 on May 2, 2011, now Pat. No. 8,766,193.

(30) Foreign Application Priority Data

May 3, 2010   (CH) ......................................... 667/10

(51) Int. Cl.
  *G01J 5/02*   (2006.01)
  *G01N 21/84*   (2006.01)
  (Continued)

(52) U.S. Cl.
  CPC ................ *G01N 21/84* (2013.01); *G01N 21/55* (2013.01); *G01N 25/72* (2013.01); *G02B 19/009* (2013.01); *G02B 19/0028* (2013.01); *G02B 19/0085* (2013.01)

(58) Field of Classification Search
  CPC ..... G01N 21/55; G01N 21/84; G02B 19/0028; G02B 19/0085; G02B 19/009
  USPC .............................................. 250/341.1–341.8
  See application file for complete search history.

(56) References Cited

U.S. PATENT DOCUMENTS 3,206,603 A   9/1965   Mauro
5,506,678 A *   4/1996   Carlsen et al. ................ 356/338
(Continued)

FOREIGN PATENT DOCUMENTS

DE   198 30 473 C1   12/1999
WO   95/16907 A1   6/1995

OTHER PUBLICATIONS

International Preliminary Report on Patentability and Written Opinion, dated Nov. 15, 2012.
(Continued)

*Primary Examiner* — Kiho Kim
(74) *Attorney, Agent, or Firm* — Sughrue Mion, PLLC

(57) ABSTRACT

A device for the contactless and nondestructive testing of a surface by measuring the infrared radiation thereof has one or more incoherent electromagnetic radiation sources (1) and a detector (14) arranged on a detection axis (9), wherein the radiation sources (1) are arranged at a radial distance from the detection axis (9), at a distance from a testing area (7). In this arrangement, a pulsed or intensity-modulated excitation radiation (2) can be generated by these radiation sources (1) and applied to the surface (6) to be tested in the testing area (7) at an inclination to the detection axis (9) in the testing area (7). The detection radiation emitted by a measuring area (8) of the surface (6) to be tested can be fed to the detector (14), wherein the detector (14) is arranged on the detection axis (9) further away spatially from the testing area (7) than the radiation sources (1). Furthermore, an imaging device (10, 12) is provided on the detection axis (9) for creating an image of the testing area (7) on the measuring area of the detector (14) that is arranged between the radiation sources (1).

5 Claims, 5 Drawing Sheets

(51) Int. Cl.
*G01N 21/55* (2014.01)
*G01N 25/72* (2006.01)
*G02B 19/00* (2006.01)

(56) References Cited

U.S. PATENT DOCUMENTS

| | | | |
|---|---|---|---|
| 5,803,606 A | 9/1998 | Petry et al. | |
| 7,498,575 B2 * | 3/2009 | Huebner et al. | 250/338.1 |
| 2002/0190212 A1 | 12/2002 | Boas et al. | |
| 2004/0022731 A1 * | 2/2004 | Bogdanov et al. | 424/9.6 |
| 2007/0040108 A1 * | 2/2007 | Wenstrand | 250/221 |
| 2008/0185520 A1 | 8/2008 | Piriou et al. | |
| 2009/0230324 A1 | 9/2009 | Gratton et al. | |

OTHER PUBLICATIONS

W.J. Parker, et al., Flash Method of Determining Thermal Diffusivity, Heat Capacity, and Thermal Conductivity, Journal of Applied Physics, vol. 32, No. 9, Sep. 1961, pp. 1679-1684.

Wing P. Leung, et al., Thermal Diffusivity in Thin Films Measured by Noncontact Single-Ended Pulsed-Laser-Induced Thermal Radiometry, IBM Research Laboratory, Mar. 1984, vol. 9, No. 3, pp. 93-95.

P. Eyerer, et al., Beruhrungslose Prufung Von Kunststoffen Mittels Photothermischer Warmewellenanalyse, Z. Werkstofftech 15, 1984, pp. 140-148.

* cited by examiner ic
DEVICE FOR THE CONTACTLESS AND NONDESTRUCTIVE TESTING OF SURFACES This is a Continuation of application Ser. No. 13/642,956 filed Oct. 23, 2012, claiming priority based on International Application No. PCT/CH2011/000097 filed May 2, 2011, claiming priority based on Swiss Patent Application No. 667/10, filed May 3, 2010, the disclosures of which are incorporated herein in their entirety by reference.

TECHNICAL FIELD

The invention relates to a device for the contactless and non-destructive testing of a surface by measuring its infrared radiation.

STATE OF PRIOR ART

The contactless testing of surfaces based on the generation and measurement of transient or periodic heating and cooling processes requires an excitation source for heating the surface to be tested as well as an infrared detector which measures the infrared radiation emitted from the heated surface. This method is called photothermy if electromagnetic radiation in the ultra-violet, optical or infrared range is used for excitation. The excitation radiation may for example come from the back of a surface, whilst the infrared radiation emitted from the surface is recorded at the front, as described by Parker et al. (1961).

In a configuration described by Leung and Tam (1984) excitation and detection take place on the same side of the surface. This configuration offers the advantage of also allowing surfaces to be tested which are accessible from one side only, and thus a much more varied range of applications.

Normally lasers are used as excitation sources for photo-thermal tests such as described by Eyrer and Busse (1984). The advantages of laser radiation for excitation are easy direction of the rays as well as high energy density due to ray bundling. These advantages permit locally precise positioning and precise metering of the excitation radiation. However, for applications outside a controlled protective environment, laser excitations suffer from major disadvantages. Photo-thermal testing requires powerful lasers (for example with 14 W optical output with pulse lengths of up to 0.1 s, see short documentation of Paintchecker modular of Messrs. Optisense) in order to achieve a measurable increase in temperature, which is dangerous to humans and animals (such lasers fall into laser classes 3 or 4). Adequate precautions are therefore necessary and the measuring system can only be operated by trained personnel. Moreover suitable laser excitations are relatively expensive. Therefore increased expenditure has to be expected in conjunction with the purchase and operation of a testing equipment with laser excitation.

In WO 95/16907 a device for photothermal testing of surfaces with laser excitation is described. The excitation beam is focussed onto a mirror which deflects the excitation beam through an opening in the sensor collecting lens onto the surface of the test piece. Apart from the disadvantages connected with using a laser source this arrangement has a further disadvantage: due to the shadow thrown by the reflecting mirror and due to the hole in the collecting lens part of the infrared radiation to be captured and emitted by the test piece gets lost.

As with laser sources alternative electromagnetic radiation sources such as flash lamps must comprise a sufficiently high energy density in order to achieve a measurable increase in temperature in the testing area of the surface to be tested. If required several flash lamps may be used in order to deposit as much energy as possible in the testing area, for example if the radiation behaviour is spread out. Due to their spatially widespread radiation behaviour the major part of the excitation radiation is lost. Therefore flash lamps are not very suitable as thermal excitation sources for the photo-thermal test procedure.

In WO 98/05949 a device is described in which at least four flash lamps of 6 kJ optical energy each are to be used for excitation of a test piece. With regard to common flash durations of 5 ms of a flash lamp this corresponds to a short-term optical power of 1.2 MW, wherein, however, only a fraction of the output is deposited in the testing area. The major part of the optical radiation does not fall within in the testing area. In order not to lose the part emitted from the back altogether, reflectors are placed behind the lamps. The infrared sensor must then be placed laterally of the excitation source(s) since no infrared radiation from the measuring area is detectable behind the excitation source(s). This lateral placement in turn has decisive disadvantages: the measuring device is spatially extended due to the parallel arrangement, and the radiation paths for excitation and detection cannot progress collinearly. The effect is that either the excitation radiation hits the surface to be tested at a flattened angle, or the detection radiation is detected at a flattened angle. The flattened angle leads to losses during heating of the surface or/and to a more extensive measuring arrangement during detection of its detection radiation.

A device with the characteristics of the preamble of claim 1 is known from the DE 198 30 473, where the infrared radiation sources are covered and exposed at intervals by a rotating covering unit.

DESCRIPTION OF THE INVENTION

Based on this state of the art the invention relates to a device for the contactless and non-destructive testing of surfaces by testing actively excited thermal processes, which can be manufactured at reduced cost and which is very easy and practical in use.

This and further requirements and advantages of the present invention are met by the features of patent claim 1.

The core of the invention consists in an arrangement of an excitation source and a reflection device for the excitation radiation emitted by the excitation source, wherein the reflection device bundles the excitation radiation emitted into wide volumes of space and applies the excitation radiation to a testing area of a surface to be tested through an opening of the reflection device and in that a radiation detector detects the infrared radiation (from now on called detection radiation) from the testing area generated by heating through the same opening.

In order to achieve as homogenous an illumination of the testing area as possible an annular excitation source is used in an especially preferred embodiment of the invention.

According to a further embodiment of the invention an infrared collecting lens or infrared mirror optics is placed in a recess in the centre of the excitation source, which focuses the detection radiation upon the infrared sensor.

This arrangement results in a number of advantages compared to known state-of-the-art devices. Since the arrangement described offers a spatially wide area of intersection between excitation radiation and detection radiation, the device is robust in relation to distance changes and tilting between the arrangement and the surface to be tested. In the embodiment of the invention in which the detection radiation is directed from the testing area to the detector through a recess in the excitation source, the device can be constructed in a very compact manner and radiation losses are minimised because both the excitation radiation and the detection radiation extend largely vertically to the testing area. In one embodiment of the invention the reflecting housing is a truncated-cone-shaped funnel from the narrowed opening of which emerges the excitation radiation and detection radiation. Due to the tapered shape the excitation radiation is bundled. As a result maximum energy efficiency is obtained which is of advantage for a compact construction and which minimises any heat losses of the device.

Advantageous embodiments and further developments are proposed in the dependent sub-claims.

In a preferred embodiment of the invention an annular flash lamp or several flash lamps arranged in a ring are used for excitation. Gas-discharge lamps are particularly suited as excitation sources due to their high efficiency and the achievable high densities. The spectrum of light generated by Xenon gas-discharge lamps substantially corresponds to the radiation curve by Planck at a temperature of approximately 5000K. The major part of the excitation radiation generated is produced in the visible spectral range between 400 nm and 800 nm, wherein a non-negligible portion of the generated excitation radiation is produced in the infrared wavelength range. The broad excitation spectrum is especially advantageous because electromagnetic radiation is absorbed independently of the spectral properties of the surface to be tested. In a preferred embodiment the incoherent light source consists of one or more LEDs. Especially advantageous is a ring-shaped arrangement of LEDs. The use of LEDs offers the advantage that electromagnetic radiation can be generated in a defined spectral range. However, only surfaces with a spectral behaviour can be tested, which permit absorption of the electromagnetic excitation radiation generated by the LEDs. This restriction may be compensated, for example, by a combination of differently coloured LEDs.

Depending upon the range of spectral sensitivity of the infrared sensor used, there is the possibility that part of the excitation radiation reflected by the test piece is detected by the infrared sensor which leads to an undesirable spectral superimposition of the excitation radiation by the heat radiation generated through heating. In order to avoid this spectral superimposition it is advantageous to place a filter device immediately in front of the flash lamp(s) for separating infrared portions of the spectrum from the radiation generated by the flash lamp(s). A preferred embodiment of the filter device consists of a housing transparent for the excitation radiation and filled with a liquid (for example water) which has an absorbing effect in the spectral sensitivity range of the infrared sensor. In an especially preferred embodiment of the invention (FIG. 8) the excitation radiation is embedded in the filter medium. If the filter medium used is a liquid, this can be pumped through a heat exchanger in a preferred embodiment and cooled, thereby ensuring active cooling of the excitation source.

SHORT DESCRIPTION OF THE DRAWINGS

Preferred embodiments of the invention will now be described by way of the drawings which merely serve as an explanation and are not to be regarded as restrictive. In the drawings.

DESCRIPTION OF THE PREFERRED EMBODIMENTS

FIGS. 1 to 9 each show a schematic sectional view through a device according to a first embodiment of the invention. Identical or similar features in all figures are marked with the same reference symbols.

Figure 1:
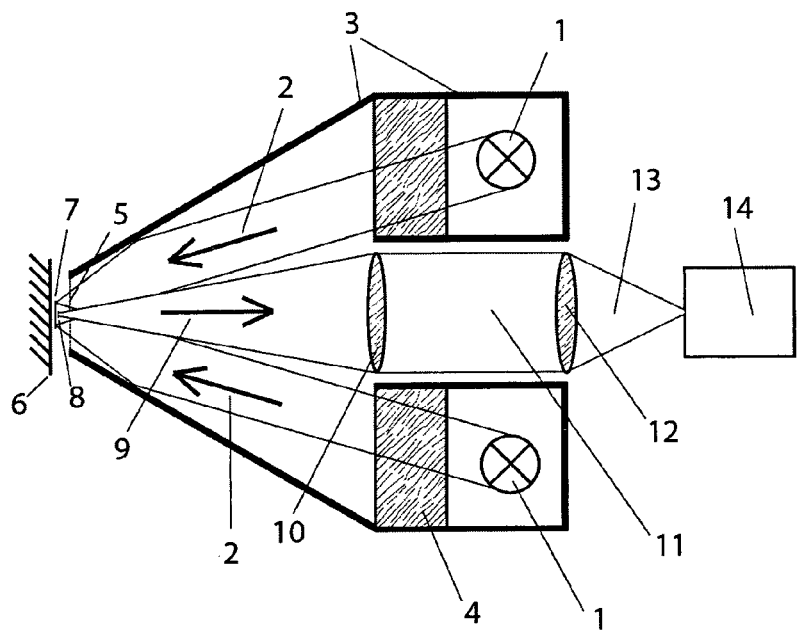
FIG. 1 shows a schematic sectional view through a device according to a first embodiment of the invention.

There is at least one radiation source 1 which at least on two opposite sides, as shown in FIG. 1, focuses excitation radiation 2 onto a testing area 7 of a surface 6 to be tested. In the very schematic parallel representation of excitation radiation 2 the function of the concentrator described below is anticipated. The excitation radiation 2 is generated by these radiation sources 1, which in particular may be one or more flash lamps arranged in a ring. The cross-section in FIG. 1 would thus be a rotation-symmetrical representation about the longitudinal axis of the device as indicated by arrow 9.

The flash lamps 1 are arranged in a torus open on one side of a reflection surface 3, which torus, at its one-sided opening, comprises a ring-shaped filter 4.

The filter device 4 is designed to separate infrared spectral portions of the light of flash lamps 1.

The excitation radiation 2 passes through these filters and is directed by the device described for bundling and directing the excitation radiation and called concentrator in the following, onto the surface 7 to be tested. In a preferred embodiment the concentrator, as shown in FIG. 1, comprises a conically narrowing reflection surface 3, wherein the angle of aperture of the cone is between 10° and 80°. This arrangement of the reflection surfaces 3 directs the light especially efficiently to the exit opening 5. In other words, the reflection surfaces 3 in this area form a hollow truncated cone open on both sides. On one side this comprises an exit opening 5 which is preferably circular or framed by a polygon course, on the opposite side it comprises the larger passing-through surface closed off by the circular filter 4 and an inner collecting lens.

The truncated cone-shaped reflection surfaces may also comprise the shape of a pyramid stump or a tapering hollow body limited by trapezes, the two openings of which are then formed by polygon courses. A truncated-cone shape is particularly meaningful for a flash lamp shaped as an annular circle, a pyramid stump is suitable for two or four flash lamps 1, a polygon course of an octagon for four or eight flash lamps 1. All these hollow, mirror-symmetrical (about axis 9) reflective bodies tapering from a large opening on the side of the flash lamp(s) 1 in direction of the testing area 7 and the opening 5 are called here a truncated cone. The opening 5 determining the testing area 7 advantageously comprises an aperture of 0.1 to 10 centimeters which for a non-round opening 5 is defined by the diameter between individual opposite portions of the polygon courses.

In a preferred embodiment the reflection surface of the concentrator consists, at least towards the inside, of a highly reflective material with a reflectivity of 20% to 100% which directs the light towards the exit opening 5 almost without any losses.

In a further preferred embodiment this highly reflective material consists of aluminium.

In a further preferred embodiment this highly reflective material consists of stainless steel which is particularly favourable with regard to manufacturing cost. If the inside surface is polished, the portion of excitation radiation directed to the testing area 7 can be further increased.

In a further preferred embodiment this highly reflective material consists of gold which comprises a particularly small emissivity in the infrared spectral range.

Due to the small emissivity of the gold surface the superimposition of the measured infrared radiation from the testing area and the inside surfaces of the concentrator is particularly small. In other words, the portion of heat radiation emitted by the reflection surfaces 3 themselves and which can also be recorded by the detector, is very small.

In order to generate a well defined measuring area, the detector 14, in a preferred embodiment, is mapped onto the surface by means of a suitable device, as described below.

The mapping device shown in FIG. 1 consists of two lenses 10 and 12 arranged on the central axis along arrow 9. Preferably the collecting lens 10 facing the testing area is not located in front of the plane which is defined by the orifice of the cone of the reflection surfaces 3. In other words, this lens 10 lies in the shade of the light portions of flash lamps 1 exiting through the filter elements 4. The collecting lens 10 collimates the detection radiation emitted by the testing area 7, which is symbolised by the arrow 9 on the longitudinal axis of the device. A further focussing lens 12 has the task of guiding the collimated radiation 13 onto the detector. In a particularly preferred embodiment the distance of the collecting lens 10 from the measuring area 7 or focussing lens 12 from the detector 14 is equal to the focal distance of the two lenses 10 or 12. The area of the parallel bundle of rays 11 is chosen so as to ensure that the detector 14 is arranged safely behind the reflection torus and thus cannot absorb any indirect radiation from the inside or outside surfaces of the reflection surfaces 3, and this is additionally ensured by a corresponding aperture opening not shown in FIG. 1 about the waist of the focussing cone 13.

Figure 2:
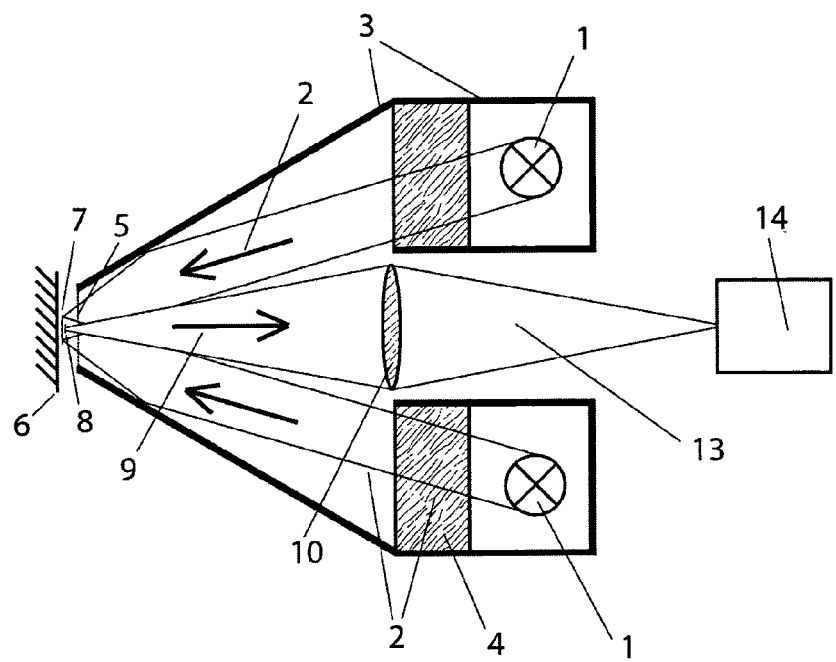
FIG. 2 shows a schematic sectional view through a device according to a second embodiment of the invention.

FIG. 2 shows an alternative mapping device consisting of only one lens 10. In an arrangement to be preferred this lens 10 is positioned in the middle between the measuring area 7 and the detector 14, wherein its fourfold focal distance corresponds the distance between measuring area 7 and detector 14. The other features of this embodiment correspond to those of the embodiment shown in FIG. 1. In particular the annular flash lamp 1 may be replaced by a plurality of individual flash lamps 1 in the reflection torus open on one side, or provision may be made for individual cylinders open on one side with inserted individual flash lamps 1 which would be possible in the representation of FIG. 2.

In a further embodiment to be preferred the detector 14 is a semiconductor detector. Semiconductor detectors are particularly sensitive and have short response times. In a particular embodiment this semiconductor detector has a sensitivity range between 2 micrometers and 20 micrometers and response times between 1 nanosecond and 1 second. Peltier or nitrogen-cooled semiconductor detectors are to be especially preferred because of their low-noise behaviour. The use of Bolometers as detectors for the detection radiation permits an especially cost-effective manufacture.

Figure 3:
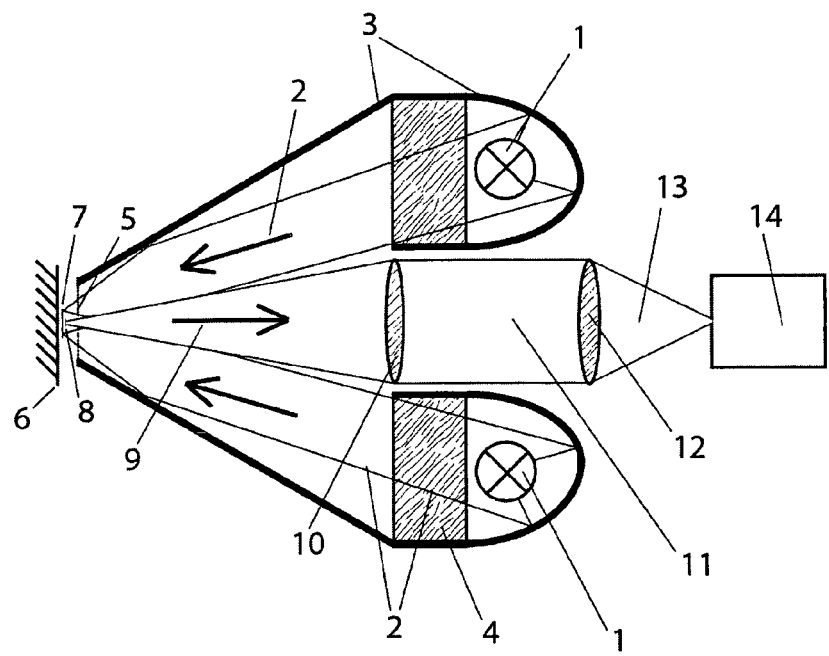
FIG. 3 shows a schematic sectional view through a device according to a third embodiment of the invention.

The part of the reflection device 3 facing away from the testing area may be implemented in an especially preferable further arrangement by curved reflection surfaces such as shown in FIG. 3. In this way the backwards radiated portion of the excitation radiation can be directed particularly efficiently to the testing area, as illustrated by the radiation progression indicated about arrow 2 of the excitation radiation.

Figure 4:
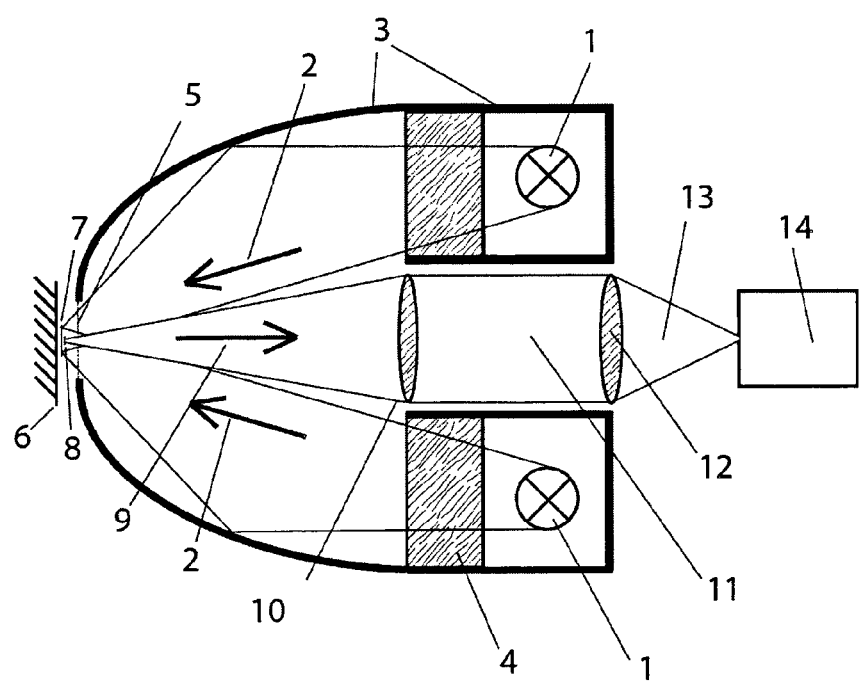
FIG. 4 shows a schematic sectional view through a device according to a fourth embodiment of the invention.

The embodiment shown in FIG. 4 comprises curved reflection surfaces 3 which direct the excitation radiation 2 particularly efficiently to the testing area, as illustrated by the radiation progression indicated about arrow 2 of the excitation radiation. The radius of curvature decreases in cross-section from a tangential constant progression at the reflection torus in the area of filters 4 down to a reflection wall extending vertically to arrow 9 in the area of opening 5 which, in the end, then defines exactly this opening 5.

Figure 5:
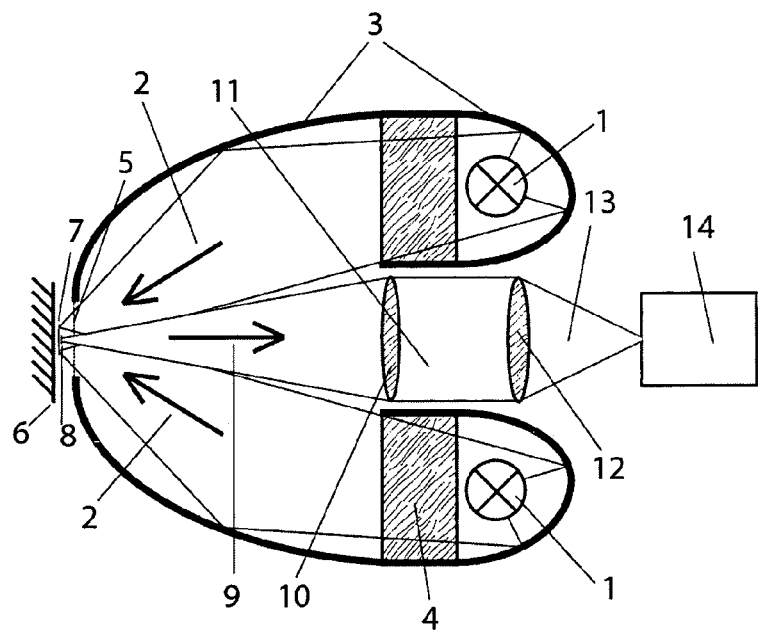
FIG. 5 shows a schematic sectional view through a device according to a fifth embodiment of the invention.

With a further preferred embodiment shown in FIG. 5 the concentrator comprises reflection surfaces 3 which can be approximated using a polynomial function, in particular a function such as $f(x)=x*x$. These direct the light especially efficiently to the exit opening 5.

With a further preferred embodiment the concentrator has hyperbolic reflection surfaces 3 in cross-section. These also direct the light especially efficiently to the exit opening 5.

With a further preferred embodiment the concentrator has elliptical reflection surfaces 3 in cross-section. These direct the light especially efficiently to the exit opening 5. In particular, a tilting of the drawn ellipsoid by between 10°-80° relative to axis 9 is especially preferred, wherein one of the two focal points is at the location of the excitation source 1 and the other focal point is at the location of the measuring area 7.

The embodiment shown in FIG. 5 comprises reflection surfaces 3 which reflect forwards and backwards.

Figure 6:
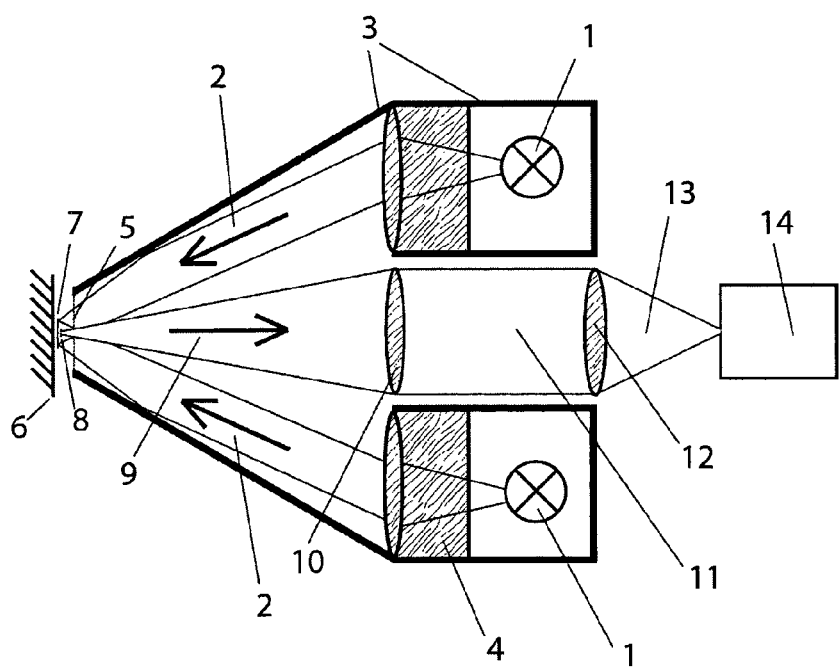
FIG. 6 shows a schematic sectional view through a device according to a sixth embodiment of the invention.

In the embodiment shown in FIG. 6 the light is directed, in addition to reflection surfaces 3, to the testing area through curved surfaces in the area of filters 4. The curved surfaces may either be attached lenses or, on the other hand, a curvature of the surface of the filter medium 4. The focal distance should be chosen such that the waist diameter of the image of the light source elements (gas discharge section, filament etc.) of the excitation radiation roughly corresponds to the size of opening 5 and lies typically between 0.01 m and 2 m depending on the distance to the surface 6 to be tested.

Figure 7:
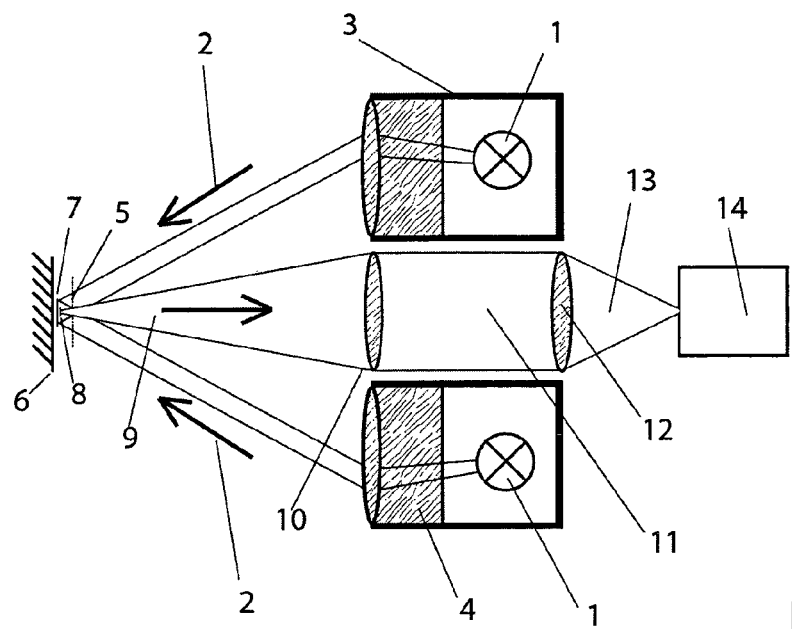
FIG. 7 shows a schematic sectional view through a device according to a seventh embodiment of the invention.

In the embodiment shown in FIG. 7 the excitation radiation is directed through these attached lenses solely on the basis of optical refraction at the same, causing a curvature of the surface of the filter medium 4 to the testing area 5.

Figure 8:
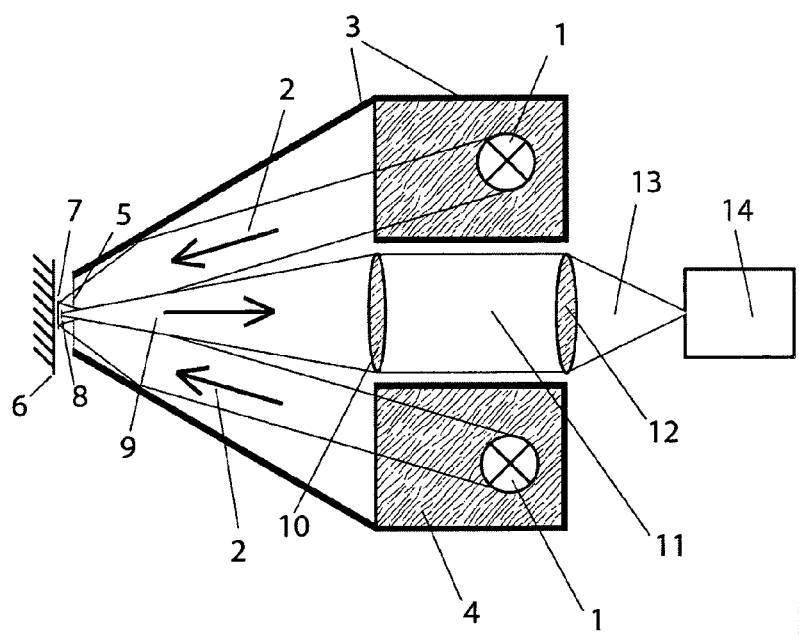
FIG. 8 shows a schematic sectional view through a device according to an eighth embodiment of the invention.

In the embodiment shown in FIG. 8 the flash lamps 1 are embedded directly into the filter medium 4.

Figure 9:
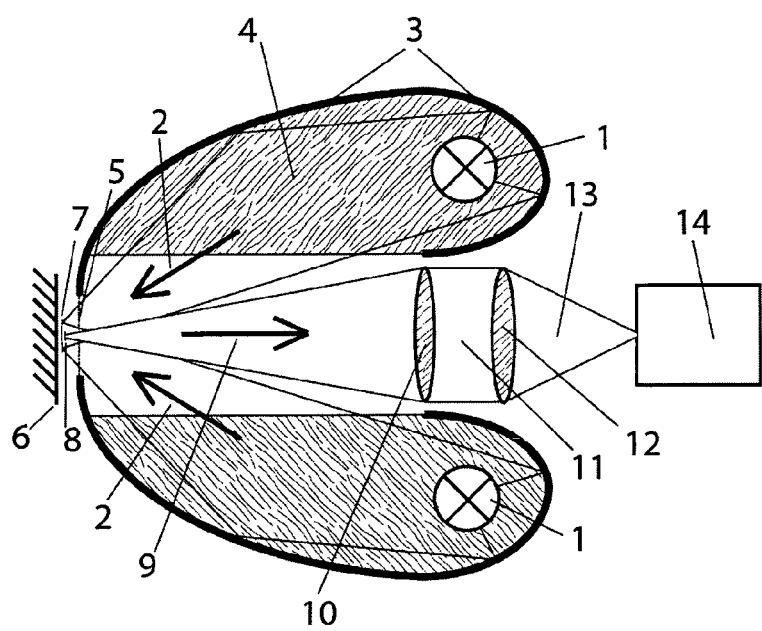
FIG. 9 shows a schematic sectional view through a device according to a ninth embodiment of the invention.

The embodiment shown in FIG. 9 represents a combination of especially preferable features with curved reflection surfaces 3 of the rearward and forward part of the reflection device and an electromagnetic excitation source 1 embedded into the filter medium 4. This embodiment permits especially efficient guiding of the electromagnetic excitation radiation 1 and a compact construction. The filter medium used may be water, in particular. The water is held in a water-tight implementation of the reflection device closed off by a pane, preferably a glass pane, which is transparent for the excitation radiation. The connection between reflection device and pane may be preferably effected by an adhesive or a rubber seal. Pressing the pane against the rubber seal may preferably be effected by a screw connection. A continual exchange of water for use as a coolant may be effected in that an inflow of water via a breakthrough is preferably effected at the bottom and in that the outflow is preferably effected via a breakthrough at the top.

In a further preferred embodiment the detection radiation 9, 11, 13 bundled by the imaging device may be fed into an optical conductor and via this optical conductor to a detector.

The various embodiments of the invention permit determination of the layer thickness of coatings as well as of their thermal properties such as diffusivity and effusivity or thermal conductivity and heat capacity, as well as the determination of adhesive properties of coatings.

LIST OF REFERENCE SYMBOLS 1 radiation source
2 excitation radiation
3 reflection surface
4 filter device
5 opening
6 surface to be tested
7 testing area
8 measuring area
9 detection radiation
10 collecting lens
11 parallel ray bundle
12 focussing lens
13 focussing cone
14 detector

The invention claimed is:

1. A device for the contactless and non-destructive testing of a test surface by measuring the infrared radiation thereof, comprising:
  one or more incoherent electromagnetic radiation sources,
  a detector providing and arranged on a detection axis and comprising a measuring area,
  a testing area defining an area to be measured of the test surface, and
  an imaging device arranged on the detection axis for mapping the testing area onto the measuring area of the detector,
  wherein the radiation sources are arranged at a radial distance from the detection axis at a distance from the testing area,
  wherein the radiation sources are adapted to generate a pulsed or intensity-modulated excitation radiation which can be directed onto the surface to be tested in the testing area,
  wherein, in response to radiation impinging onto the surface to be tested in the testing area, detection radiation is emitted by the measuring area of the surface to be tested and fed to the detector,
  wherein the radiation sources are arranged in a housing having the form of a torus or polygon course open on one side towards the testing area,
  wherein the excitation radiation from the radiation sources is fed to the testing area at an inclination to the detection axis,
  wherein the detector on the detection axis is arranged spatially further away from the testing area than the radiation sources,
  wherein the imaging device is arranged between the radiation sources,
  wherein one or more optical filter devices are arranged between the radiation sources and the testing area, through which the excitation radiation is guidable to the testing area, wherein the filter devices are designed to absorb one or more spectral ranges of the generated excitation radiation,
  wherein the one or more optical filters are provided as a ring-shaped or polygon-shaped filter at the one-sided opening of the housing.

2. The device according to claim 1, wherein the opening determining the testing area comprises an aperture of between 0.1 and 10 centimeters.

3. The device according to claim 1, wherein the imaging device directs the detection radiation passing through the opening of the reflection device and emitted by the testing area to the detector in the measuring area defined by the imaging device.

4. The device according to claim 1, wherein the imaging device comprises a collecting lens which collects the detection radiation emitted by the measuring area and converts it into a parallel bundle of rays, the collecting lens being arranged between the torus shaped or polygon course shaped housing, so that the detector is arranged safely behind the reflection housing and thus cannot absorb any indirect radiation from the inside or outside surfaces of the reflection surfaces.

5. The device according to claim 1, wherein the imaging device comprises a focusing lens which maps the detection radiation onto the detector.

* * * * *